(12) United States Patent
Sonobe et al.

(10) Patent No.: US 11,123,305 B2
(45) Date of Patent: *Sep. 21, 2021

(54) PATCH

(71) Applicant: HISAMITSU PHARMACEUTICAL CO., INC., Tosu (JP)

(72) Inventors: Atsushi Sonobe, Tsukuba (JP); Takashi Yasukochi, Tsukuba (JP); Yasunori Takada, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/008,704

(22) Filed: Jun. 14, 2018

(65) Prior Publication Data

US 2018/0289631 A1 Oct. 11, 2018

Related U.S. Application Data

(63) Continuation-in-part of application No. 14/416,983, filed as application No. PCT/JP2013/070197 on Jul. 25, 2013, now Pat. No. 10,022,445.

(30) Foreign Application Priority Data

Jul. 26, 2012 (JP) .................................. 2012-165793
Apr. 4, 2013 (JP) .................................. 2013-078583

(51) Int. Cl.
| A61K 9/70 | (2006.01) |
| A61K 47/10 | (2017.01) |
| A61K 47/12 | (2006.01) |
| A61K 47/14 | (2017.01) |
| A61K 31/407 | (2006.01) |

(52) U.S. Cl.
CPC .......... *A61K 9/7069* (2013.01); *A61K 9/7053* (2013.01); *A61K 31/407* (2013.01); *A61K 47/10* (2013.01); *A61K 47/14* (2013.01); *A61K 9/7061* (2013.01); *A61K 47/12* (2013.01)

(58) Field of Classification Search
CPC .. A61K 9/7038; A61K 9/7046; A61K 9/7053; A61K 9/7061; A61K 9/7069; A61K 9/7076; A61K 31/407; A61K 47/14; A61K 47/10; A61K 47/12
See application file for complete search history.

(56) References Cited

U.S. PATENT DOCUMENTS

| 5,830,497 A | 11/1998 | Yamanaka et al. |
| 6,620,429 B1 | 9/2003 | Mueller |

(Continued)

FOREIGN PATENT DOCUMENTS

| CN | 1372463 A | 10/2002 |
| EP | 0508400 A1 * | 10/1992 |

(Continued)

OTHER PUBLICATIONS

International Search Report dated Sep. 10, 2013 in PCT/JP13/070197 Filed Jul. 25, 2013.

*Primary Examiner* — Hong Yu
(74) *Attorney, Agent, or Firm* — Oblon, McClelland, Maier & Neustadt, L.L.P.

(57) ABSTRACT

In a patch comprising a support layer and an adhesive agent layer, the adhesive agent layer comprises free asenapine, a maleic acid alkali salt, and a rubber-based adhesive agent.

20 Claims, 1 Drawing Sheet

(56) References Cited

U.S. PATENT DOCUMENTS

| | | | |
|---|---|---|---|
| 10,022,445 B2 * | 7/2018 | Sonobe | A61K 47/12 |
| 2001/0051166 A1 | 12/2001 | Luo et al. | |
| 2004/0142024 A1 | 7/2004 | Chono et al. | |
| 2006/0204486 A1 * | 9/2006 | Pyke | A61K 9/2009 424/94.2 |
| 2011/0028880 A1 | 2/2011 | Uchida et al. | |
| 2013/0315977 A1 * | 11/2013 | Maeda | A61K 9/7053 424/443 |
| 2015/0164862 A1 | 6/2015 | Suzuki et al. | |
| 2015/0202183 A1 | 7/2015 | Suzuki et al. | |

FOREIGN PATENT DOCUMENTS

| | | |
|---|---|---|
| JP | 02-255611 | 10/1990 |
| JP | 02-255612 | 10/1990 |
| JP | 2002-509874 | 4/2002 |
| JP | 2009-242303 | 10/2009 |
| WO | WO 20091107479 | 9/2009 |
| WO | WO 2010/127674 | 11/2010 |
| WO | WO 2011/136283 | 11/2011 |
| WO | WO 2012/105624 A1 * | 8/2012 |

\* cited by examiner

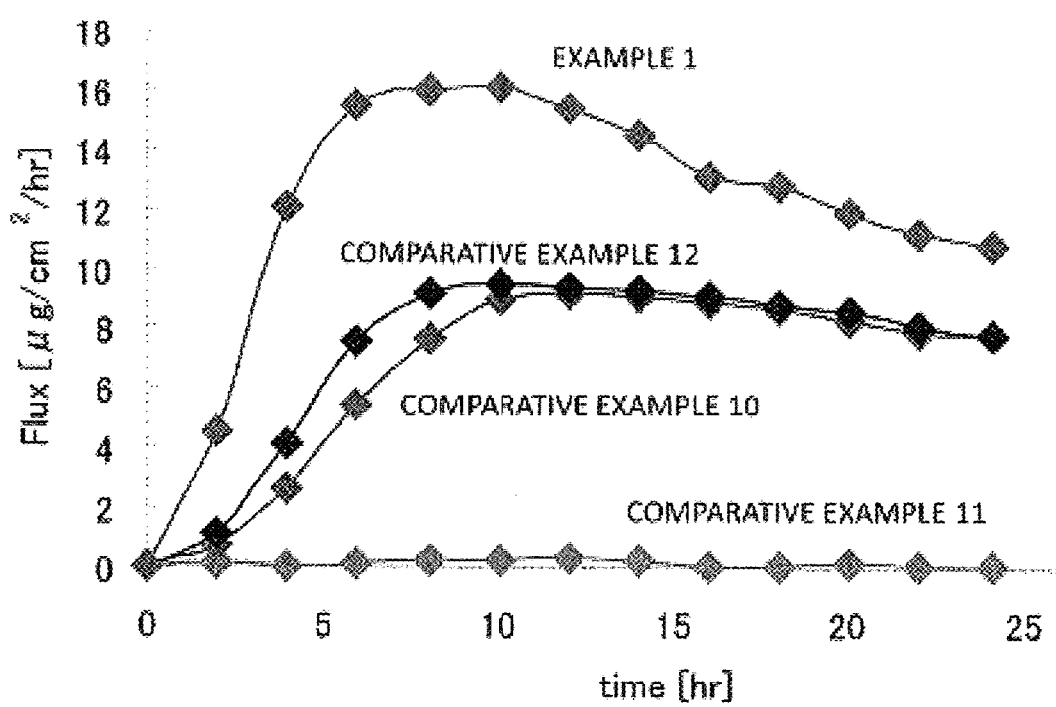

PATCH

CROSS-REFERENCE TO RELATED APPLICATIONS

The present application is a continuation-in-part of U.S. application Ser. No. 14/416,983, filed Jan. 23, 2015, the entire contents of which are incorporated herein by reference. U.S. application Ser. No. 14/416,983 is a National Stage of International Application No. PCT/JP2013/070197 filed Jul. 25, 2013, which is based upon and claims the benefit of priority to Japanese Applications No. 2013-078583, filed Apr. 4, 2013 and No. 2012-165793, filed Jul. 26, 2012. The present application claims the benefit of priority to Japanese Applications No. 2013-078583 and No. 2012-165793, U.S. application Ser. No. 14/416,983, and International Application No. PCT/JP2013/070197.

TECHNICAL FIELD

The present invention relates to a patch. Specifically, the present invention relates to a patch using asenapine as a drug.

BACKGROUND ART

Asenapine (trans-5-chloro-2-methyl-2,3,3a,12b-tetrahydro-1H-dibenz[2,3:6,7]oxepino[4,5-c]pyrrole) is a compound having a central nervous system (CNS)-suppressing activity, an anti-histamine activity, and an anti-serotoninergic activity. Asenapine is known as a drug for use in the treatment of central nervous system diseases such as schizophrenia.

For example, International Publication No. WO2010/127674 (PTL 1) describes pharmaceutical preparations containing asenapine, in the form of topical agents such as sprays, aerosols, patches, and ointments. Moreover, International Publication No. WO2011/136283 (PTL 2) describes a transdermal preparation containing a skin irritation suppressant including a cholesterol compound, a drug, and a pharmaceutical ingredient. PTL 2 cites asenapine as the drug. However, a patch containing asenapine in an adhesive agent layer has a problem that the skin permeability of asenapine is not sufficient, so that it is difficult to keep the plasma concentration of asenapine at a therapeutically effective level.

CITATION LIST

Patent Literature

[PTL 1] International Publication No. WO2010/127674
[PTL 2] International Publication No. WO2011/136283

SUMMARY OF INVENTION

Technical Problems

The present inventors have found that, in a patch containing asenapine, the use of a rubber-based adhesive agent as an adhesive base agent in an adhesive agent layer can improve the release of asenapine from the adhesive agent layer, making it possible to improve the skin permeability of asenapine. On the other hand, the inventors have found that the patch has a problem that the adhesion force of an adhesive agent layer is decreased in the case where asenapine and the rubber-based adhesive agent are incorporated into the adhesive agent layer.

The present invention has been made in view of the problems of the conventional techniques, and an object of the present invention is to provide a patch comprising an adhesive agent layer having a sufficiently strong adhesion force, the patch being excellent in releasability and skin permeability of asenapine from the adhesive agent layer.

Solution to Problems

The present inventors have conducted earnest study to achieve the above object. As a result, the inventors have found that incorporating a combination of free asenapine as a drug, a rubber-based adhesive agent as an adhesive base agent, and a maleic acid alkali salt into an adhesive agent layer of a patch comprising a support layer and the adhesive agent layer enables the release and the skin permeability of asenapine from the adhesive agent layer to be sufficiently high, and suppresses a decrease in an adhesion force due to a combination of asenapine with the rubber-based adhesive agent, so that a sufficient adhesion force can be exhibited. These findings have led to the completion of the present invention.

Specifically, a patch of the present invention is a patch comprising a support layer and an adhesive agent layer, characterized in that the adhesive agent layer comprises free asenapine, a maleic acid alkali salt, and a rubber-based adhesive agent.

Moreover, in the patch of the present invention, a mass ratio of the free asenapine to the maleic acid alkali salt (free asenapine:maleic acid alkali salt) in the adhesive agent layer is preferably 1:0.1 to 1:3. Further, in the patch of the present invention, a content of the rubber-based adhesive agent in the adhesive agent layer is preferably 10 to 50% by mass.

Additionally, in the patch of the present invention, the rubber-based adhesive agent is preferably at least one selected from the group consisting of styrene-isoprene-styrene block copolymers, polyisobutylene, and silicone rubbers. Furthermore, in the patch of the present invention, the maleic acid alkali salt is preferably disodium maleate and/or sodium maleate.

In addition, in the patch of the present invention, the free asenapine and the maleic acid alkali salt are preferably generated from an asenapine maleic acid salt and an alkali metal ion-containing desalting agent in the adhesive agent layer.

Advantageous Effects of Invention

The present invention makes it possible to provide a patch comprising an adhesive agent layer having a sufficiently strong adhesion force, the patch being excellent in releasability and skin permeability of asenapine from the adhesive agent layer.

BRIEF DESCRIPTION OF DRAWING

FIG. 1 is a graph showing a relation between the elapsed time from the application and skin permeation rates of asenapine in patches obtained in Example 1 and Comparative Examples 10 to 12.

DESCRIPTION OF EMBODIMENTS

Hereinafter, the present invention will be described in detail based on preferred embodiments thereof. A patch of the present invention is a patch comprising a support layer and an adhesive agent layer, wherein the adhesive agent layer comprises free asenapine, a maleic acid alkali salt, and a rubber-based adhesive agent.

The patch of the present invention comprises: the support layer; and the adhesive agent layer arranged on at least one surface of the support layer. As the support layer according to the present invention, conventionally known ones can be used as appropriate. Examples of the material of such a support layer include synthetic resins such as polyethylene, polypropylene, polybutadiene, ethylene-vinyl acetate copolymers, vinyl acetate-vinyl chloride copolymers, polyvinyl chloride, polyamides such as nylons, polyesters, cellulose derivatives, and polyurethane. Moreover, examples of the form of the support layer include films; sheets; sheet-shaped porous articles; sheet-shaped foamed articles; fabrics such as woven fabrics, knitted fabrics, and nonwoven fabrics; laminates thereof; and the like. In the present invention, the thickness of the support layer is not particularly limited, but normally a preferable thickness is approximately 2 to 3000 μm.

Additionally, the patch of the present invention may further comprise a release liner on a surface of the adhesive agent layer, the surface being opposite to the support layer. The release liner only needs to be capable of covering the adhesive agent layer before the patch is used, and removable by releasing when used. Specific examples of the release liner include polyesters such as polyethylene terephthalate and polyethylene naphthalate; polyolefins such as polyethylene and polypropylene; films of polyvinyl chloride, polyvinylidene chloride, and the like; laminate films of woodfree paper and polyolefins; films of nylons, aluminium, and the like; and other similar materials. From the viewpoint of facilitating the releasing from the adhesive agent layer, these release liners used are preferably subjected to surface coating (releasing process) using a release agent such as silicone or polytetrafluoroethylene.

The adhesive agent layer according to the present invention comprises free asenapine, a maleic acid alkali salt, and a rubber-based adhesive agent. The thickness of such an adhesive agent layer is not particularly limited, and is normally approximately 10 to 1000 μm.

<Asenapine>

The asenapine according to the present invention refers to trans-5-chloro-2-methyl-2,3,3a,12b-tetrahydro-1H-dibenz[2,3:6,7]oxepino[4,5-c]pyrrole. The asenapine has a central nervous system (CNS)-suppressing activity, an anti-histamine activity, and an anti-serotoninergic activity, and is normally known as a drug for use in the treatment of central nervous system diseases such as schizophrenia.

In the present invention, such asenapine has to be in a free form: free asenapine. The present inventors have found that simply incorporating asenapine and/or a pharmaceutically acceptable salt thereof into an adhesive agent layer using a rubber-based adhesive agent as an adhesive base agent significantly decreases the adhesion force of the adhesive agent layer; in contrast, the use of free asenapine as a drug in combination with a maleic acid alkali salt and a rubber-based adhesive agent sufficiently increases the adhesion force of the adhesive agent layer.

The free asenapine according to the present invention may be added in the form of free asenapine at the time of production of a patch, or may be generated (synthesized) from a pharmaceutically acceptable salt of asenapine in the adhesive agent layer from the viewpoints of handleability and stability of the raw material. Alternatively, the free asenapine may be a mixture of the two. An example of the method for generating (synthesizing) the free asenapine from a pharmaceutically acceptable salt of asenapine (hereinafter sometimes referred to as asenapine salt) includes a method in which the asenapine salt is desalted by blending the asenapine salt and a metal ion-containing desalting agent (neutralizing agent) in the adhesive agent layer composition at the time of production of a patch.

The asenapine salt is preferably an acid adduct from the viewpoint that it is easily desalted with the metal ion-containing desalting agent. Examples of the acid include monobasic acids such as hydrochloric acid, hydrobromic acid, and methanesulfonic acid; and polybasic acids such as fumaric acid, maleic acid, citric acid, and tartaric acid. One of these may be used alone, or two or more thereof may be used in combination. Among these, the asenapine salt is particularly preferably a maleic acid salt (asenapine maleic acid salt) from the viewpoint that the free asenapine and the maleic acid alkali salt according to the present invention can be generated when an alkali metal ion-containing desalting agent is used as the metal ion-containing desalting agent.

Moreover, examples of the metal ion-containing desalting agent include metal hydroxides, acetic acid metal salts, and the like. Examples of the metal include sodium, potassium, magnesium, and the like. One of these may be used alone, or two or more thereof may be used in combination. Among these, the metal ion-containing desalting agent is preferably alkali metal ion-containing desalting agents, particularly preferably sodium hydroxide and sodium acetate, from the viewpoints that: they are easy to handle during production, that when an asenapine maleic acid salt is used as the asenapine salt, the free asenapine and the maleic acid alkali salt according to the present invention can be generated, and that the stability over time of the free asenapine is further improved.

In the case where the free asenapine according to the present invention is generated from the asenapine salt, the amount of the metal ion-containing desalting agent blended is preferably an amount of 0.5 to 6 equivalents, more preferably 0.75 to 4 equivalents, to the asenapine salt in terms of acid-base equivalence. If the amount of the metal ion-containing desalting agent blended is less than the lower limit, it becomes difficult to generate the free asenapine in a sufficient amount, so that the adhesion force of the adhesive agent layer tends to be decreased. On the other hand, if the amount exceeds the upper limit, the stability over time of the free asenapine tends to be decreased.

In the adhesive agent layer according to the present invention, a content of the free asenapine is preferably 1 to 15% by mass, more preferably 1.5 to 12% by mass, and further preferably 2 to 10% by mass, relative to the entire adhesive agent layer, although the content cannot be generalized because it depends on the treatment target and purpose. If the content of the free asenapine is less than the lower limit, the skin permeation amount tends to be decreased, so that the area of the patch needs to be increased. On the other hand, if the content exceeds the upper limit, a local adverse effect such as skin irritation tends to occur, or adhesive properties such as tackiness and adhesive force to skin tend to be decreased.

<Maleic Acid Alkali Salt>

The adhesive agent layer according to the present invention comprises a maleic acid alkali salt. The present inventors have found that simply incorporating a maleic acid alkali salt into an adhesive agent layer using a rubber-based adhesive agent as an adhesive base agent decreases the adhesion force of the adhesive agent layer; in contrast, the use of free asenapine, a maleic acid alkali salt, and a rubber-based adhesive agent in combination enables the adhesive agent layer to exhibit a sufficiently strong adhesion force.

The maleic acid alkali salt may be added as a maleic acid alkali salt at the time of production of a patch, or may be generated from a maleic acid salt and the alkali metal ion-containing desalting agent in the adhesive agent layer from the viewpoints of handleability and stability of the raw material. Alternatively, the maleic acid alkali salt may be a mixture of the two. An example of the method for generating such a maleic acid alkali salt includes a method in which the maleic acid salt is desalted by blending the maleic acid salt with the alkali metal ion-containing desalting agent in the adhesive agent layer composition at the time of production of a patch.

The maleic acid salt is preferably an asenapine maleic acid salt from the viewpoint that the free asenapine and the maleic acid alkali salt can be generated. Moreover, in the case where the maleic acid alkali salt is generated from the maleic acid salt and the alkali metal ion-containing desalting agent, the amount of the alkali metal ion-containing desalting agent blended is the same as the above-described amount of the metal ion-containing desalting agent blended with the maleic acid salt in terms of acid-base equivalence.

Examples of such a maleic acid alkali salt include disodium maleate, sodium maleate, dipotassium maleate, potassium maleate, and the like. The maleic acid alkali salt may be a hydrate having crystallized water. One of these may be used alone, or two or more thereof may be used in combination. Among these, disodium maleate and/or sodium maleate are preferable from the viewpoints that the handleability is excellent, and that a desalting reaction tends to readily take place.

In the adhesive agent layer according to the present invention, a content of the maleic acid alkali salt is preferably 0.5 to 15% by mass, more preferably 1 to 10% by mass, relative to the entire adhesive agent layer. Further, in the patch of the present invention, amass ratio of the free asenapine to the maleic acid alkali salt (free asenapine: maleic acid alkali salt) in the adhesive agent layer is preferably 1:0.1 to 1:3, more preferably 1:0.25 to 1:2. If the content of the maleic acid alkali salt is less than the lower limit, the release of asenapine from the adhesive agent layer and the the adhesion force of the adhesive agent layer tend to be decreased. On the other hand, if the content exceeds the upper limit, a local adverse effect such as skin irritation tends to occur.

<Rubber-Based Adhesive Agent>

In the patch of the present invention, a rubber-based adhesive agent has to be used as the adhesive base agent. Examples of the rubber-based adhesive agent include natural rubbers, polyisobutylene, alkyl vinyl ether (co)polymers, polyisoprene, polybutadiene, styrene-butadiene copolymers, styrene-isoprene copolymers, styrene-isoprene-styrene block copolymers, silicone rubbers, and the like. One of these may be used alone, or two or more thereof may be used in combination. Especially, the rubber-based adhesive agent according to the present invention is preferably at least one selected from the group consisting of styrene-isoprene-styrene block copolymers, polyisobutylene, and silicone rubbers, more preferably a styrene-isoprene-styrene block copolymer and polyisobutylene, from the viewpoints that the release of asenapine from the adhesive agent layer is further improved and that the adhesive agent layer tends to exhibit a more sufficient adhesion force. Additionally, in this case, a mass ratio of the styrene-isoprene-styrene block copolymer to the polyisobutylene (styrene-isoprene-styrene block copolymer:polyisobutylene) is particularly preferably 15:2 to 2:15.

A content of such a rubber-based adhesive agent is preferably 10 to 50% by mass, more preferably 12 to 40% by mass, relative to the entire adhesive agent layer. Moreover, in the patch of the present invention, a mass ratio of the free asenapine to the rubber-based adhesive agent (free asenapine:rubber-based adhesive agent) in the adhesive agent layer is preferably 1:17 to 1:1.2, more preferably 1:14 to 1:1.4. If the content of the rubber-based adhesive agent is less than the lower limit, the adhesiveness of the patch to skin tends to be decreased. On the other hand, if the content exceeds the upper limit, the releasability of asenapine from the adhesive agent layer is decreased, so that it tends to be difficult to achieve a sufficient skin permeability.

<Additive etc.>

In the patch of the present invention, in the case where the free asenapine is generated from the asenapine salt in the adhesive agent layer, the adhesive agent layer according to the present invention may further comprise the asenapine salt which is blended at the time of production of a patch, but which remains without turning into free asenapine. In the case where the adhesive agent layer according to the present invention further comprise such an asenapine salt, a content thereof in terms of free asenapine is preferably 3.5% by mass or less, more preferably 2% by mass or less, relative to the entire adhesive agent layer. If the content of the asenapine salt exceeds the upper limit, the releasability and the skin permeability of asenapine from the adhesive agent layer tend to be decreased.

Moreover, in the patch of the present invention, in the case where the free asenapine and/or the maleic acid alkali salt are generated by the desalting (neutralization) in the adhesive agent layer, the adhesive agent layer according to the present invention may further comprise the metal ion-containing desalting agent (preferably the alkali metal ion-containing desalting agent), and a metal salt other than the maleic acid alkali salt generated by the desalting. Although the metal salt is determined based on the combination of the asenapine salt and the metal ion-containing desalting agent, examples of the metal salt include at least one selected from the group consisting of metal chlorides, metal bromides, metal iodides, and organic acid metal salts. More specific examples thereof include sodium chloride, magnesium chloride, potassium chloride, sodium citrate, sodium oxalate, sodium tartrate, sodium bromide, sodium succinate, and the like. In the case where the adhesive agent layer according to the present invention further comprises such a metal salt, a content thereof is preferably 4% by mass or less relative to the entire adhesive agent layer from the viewpoint that if the content of the metal salt in the adhesive agent layer is higher, the metal salt is dispersed inhomogeneously, so that the adhesion force of the adhesive agent layer tends to be decreased.

The adhesive agent layer according to the present invention may further comprise, as necessary, a drug other than asenapine; an adhesive base agent other than the rubber-based adhesive agent; and additives such as a tackifier, a softener, a stabilizer, and an absorption enhancer (permeation enhancer), unless the effects of the present invention are not impaired.

Examples of the adhesive base agent other than the rubber-based adhesive agent include (meth)acrylic ester (co)polymers, silicone polymers other than the silicone rubbers, polyurethane-based adhesive agents, and the like. The (meth)acrylic ester (co)polymers are (co)polymers containing acrylic ester and/or methacrylic ester as a main monomer unit(s) and, if necessary, a secondary monomer copolymerized therewith. Examples of the main monomer include methyl (meth)acrylate, ethyl (meth)acrylate, butyl (meth)acrylate, hexyl (meth)acrylate, heptyl (meth)acrylate, octyl (meth)acrylate, 2-ethylhexyl (meth)acrylate, and the like. One of these may be used alone, or two or more thereof may be used in combination. Moreover, the secondary monomer is not particularly limited, but examples thereof include N-vinyl-2-pyrrolidone, methylvinyl pyrrolidone, (meth) acrylic acid, vinyl acetate, and the like. A content of the adhesive base agent other than the rubber-based adhesive agent is preferably 30% by mass or less relative to the entire adhesive agent layer from the viewpoint that the skin permeability of asenapine tends to be decreased if the adhesive agent layer according to the present invention further comprises such an adhesive base agent.

Examples of the tackifier include alicyclic saturated hydrocarbon resins; rosin and rosin derivatives such as rosin glycerin ester, hydrogenated rosin, hydrogenated rosin glycerin ester, rosin pentaerythritol ester, and maleic rosin; terpene-based tackifier resins; petroleum-based tackifier resins; and the like. One of these may be used alone, or two or more thereof may be used in combination. In the present invention, petroleum-based tackifier resins are preferably used from the viewpoints of pharmaceutical physical properties such as cohesion and adhesion. In the case where the adhesive agent layer according to the present invention comprises such a tackifier, a content thereof is preferably such that amass ratio of the rubber-based adhesive agent to the tackifier (rubber-based adhesive agent:tackifier) is 1:6 to 1.5:1 (more preferably 1:5 to 1:1). If the content of the tackifier is less than the lower limit, the adhesive force to skin tends to be decreased. On the other hand, if the content exceeds the upper limit, the cohesive force of the adhesive agent layer tends to be decreased, and the pain during peeling off tends to be increased.

Examples of the softener include paraffin oils such as liquid paraffin; animal oils such as squalane and squalene; vegetable oils such as almond oil, olive oil, camellia oil, castor oil, tall oil, and peanut oil; silicone oils; liquid rubbers such as polybutene and polyisoprene; and the like. One of these may be used alone, or two or more thereof may be used in combination. In the present invention, from the viewpoints of pharmaceutical physical properties, liquid paraffin is preferably used. In the case where the adhesive agent layer according to the present invention comprises such a softener, a content thereof is preferably such that a mass ratio of the rubber-based adhesive agent to the softener is (rubber-based adhesive agent:softener) is 1:6 to 5:1 (more preferably 1:4 to 3:1). If the content of the softener is less than the lower limit, the adhesive force to skin tends to be decreased. On the other hand, if the content exceeds the upper limit, the cohesive force of the adhesive agent layer tends to be decreased, and the adhesive agent layer or stickiness tends to remain on skin after peeling off.

Examples of the stabilizer that can be suitably used include tocopherol and ester derivatives thereof, ascorbic acid and ester derivatives thereof, dibutylhydroxytoluene, butylhydroxyanisole, and the like. One of these may be used alone, or two or more thereof may be used in combination. In the present invention, from the viewpoints of pharmaceutical physical properties, appearance, and drug-stabilizing effect, dibutylhydroxytoluene is more preferably used. In the case where the adhesive agent layer according to the present invention comprises such a stabilizer, a content thereof is preferably 0.1 to 3% by mass, more preferably 0.15 to 3% by mass, relative to the entire adhesive agent layer. If the content of the stabilizer is less than the lower limit, the stability of each component in the patch tends to be decreased. On the other hand, if the content exceeds the upper limit, the cohesive force of the adhesive agent layer tends to be decreased.

Examples of the absorption enhancer that can be suitably used include aliphatic alcohols such as isostearyl alcohol; fatty acids such as capric acid; fatty acid derivatives such as propylene glycol monolaurate, isopropyl myristate, isopropyl palmitate, and lauric acid diethanolamide; glycols such as propylene glycol and polyethylene glycol; and the like. One of these may be used alone, or two or more thereof may be used in combination. In the present invention, from the viewpoint that the skin permeability of asenapine tends to be remarkably improved, propylene glycol monolaurate or isopropyl palmitate is preferably used, and isopropyl palmitate is more preferably used.

In the case where the adhesive agent layer according to the present invention comprises such an absorption enhancer, a content thereof is preferably 2 to 40% by mass relative to the entire adhesive agent layer. Moreover, in the case where the absorption enhancer is the isopropyl palmitate, a content thereof is preferably 2 to 15% by mass, more preferably 5 to 12% by mass, relative to the entire adhesive agent layer. If the content of the absorption enhancer is less than the lower limit, the skin permeability of asenapine tends to be decreased. On the other hand, if the content exceeds the upper limit, the absorption enhancer is separated from the adhesive agent layer, so that the adhesion of the adhesive agent layer tends to be impaired, or a local adverse effect such as skin irritation tends to occur.

Further, in the case where the adhesive agent layer according to the present invention further comprises these additives, the total content is preferably 85% by mass or less relative to the entire adhesive agent layer.

In addition, the adhesive agent layer according to the present invention preferably comprises substantially no water. Since the adhesive agent layer according to the present invention is constituted mainly of hydrophobic components, if the water content exceeds 10% by mass, water is separated from the adhesive agent layer, so that the adhesion of the adhesive agent layer tends to be impaired. Here, the phrase comprises substantially no water means that no water is intentionally added at the time of production, and that the water content determined by a measurement according to the Karl Fischer's method based on The Japanese Pharmacopoeia is less than 10% relative to the entire adhesive agent layer.

<Method for Producing Patch>

The patch of the present invention is not particularly limited, and can be produced by employing a known method for producing a patch as appropriate. For example, first, the free asenapine, the maleic acid alkali salt, the rubber-based adhesive agent, and, as necessary, the additives, a solvent, or the like are kneaded according to an ordinary method to thus obtain a homogeneous adhesive agent layer composition. Then, this adhesive agent layer composition is applied onto a surface (normally on one surface) of the support layer to a predetermined thickness, followed by, as necessary, heating and drying to remove the solvent, and the resultant is cut into a desired size, so that the patch of the present invention can be obtained.

Examples of the solvent include toluene, ethanol, methanol, ethyl acetate, and the like. One of these may be used alone, or two or more thereof may be used in combination. Moreover, the heating conditions can be selected as appropriate, depending on the solvent. The temperature condition is preferably normally 60 to 120° C., and the heating period is preferably normally 2 to 30 minutes.

In this event, in the case where the free asenapine used is generated from an asenapine salt, for example, the asenapine salt and the metal ion-containing desalting agent are blended in the adhesive agent layer composition to generate free asenapine, so that the resulting adhesive agent layer can comprise the free asenapine. Moreover, in the case where the maleic acid alkali salt used is generated from a maleic acid salt and an alkali metal ion-containing desalting agent, for example, the maleic acid salt and the alkali metal ion-containing desalting agent are blended in the adhesive agent layer composition to generate a maleic acid alkali salt, so that the resulting adhesive agent layer can comprise the maleic acid alkali salt. Further, in the cases, from the viewpoint that the free asenapine and the maleic acid alkali salt can be generated, it is preferable to blend an asenapine maleic acid salt and the alkali metal ion-containing desalting agent in the adhesive agent layer composition.

Moreover, the method for producing a patch of the present invention may further comprise a step of laminating the release liner to a surface of the adhesive agent layer, the surface being opposite to the support layer. Otherwise, first, the adhesive agent layer composition is applied onto one surface of the release liner to form an adhesive agent layer of a predetermined thickness. Then, the support layer is laminated to a surface of the adhesive agent layer, the surface being opposite to the release liner. The resultant is cut into a predetermined shape. In this way, the patch of the present invention may be obtained.

EXAMPLES

Hereinafter, the present invention will be more specifically described on the basis of Examples and Comparative Examples. However, the present invention is not limited to the following Examples. Note that each patch obtained in Examples and Comparative Examples was subjected to peel test, drug release test in water, and skin permeation test respectively by methods illustrated below.

(Peel Test (180° Peel Adhesion Force Test))

First, three test pieces each 1 cm×5 cm were cut from each patch. After release liners were released off from the three test pieces, each test piece was applied to a Bakelite plate and left standing for 30 minutes. Subsequently, the test piece was peeled off at 180° from the Bakelite plate at a speed of 30 cm/min. The peel strength was measured at 5 points at intervals of 5 mm starting from a position 5 mm away from a position where the peeling was started. The average value was set as an adhesion force [unit: gF/cm].

(Drug Release Test in Water)

First, each patch was cut to a size of 3.16 cm×3.16 cm. After a release liner was released off, the resultant was set to a rotating cylinder of a dissolution test apparatus (constant-temperature water bath type dissolution tester, manufactured by Toyama Sangyo Co., Ltd.), so that the adhesive agent layer was located at the outer side. Then, a round-bottom flask containing 900 ml of a dissolution test fluid (second fluid for dissolution test described in The Japanese Pharmacopoeia) was set to the dissolution test apparatus, and the temperature was set at 32° C. The rotating cylinder was immersed into the dissolution test fluid. While the rotating cylinder was being rotated at a speed of 50 rpm, 10 ml of the dissolution test fluid was sampled every predetermined period until 24 hours elapsed from the start of the rotation. A total mass (amount released into water) of free asenapine released into water for 24 hours from the start of the rotation was measured by high-performance liquid chromatography. Based on a mass of asenapine in terms of free asenapine contained in the adhesive agent layer before the test (initial amount of asenapine), a proportion released into water (drug release rate) [%] was calculated according to the following formula:

proportion released into water [%]=(amount released into water/initial amount of asenapine)×100.

(Skin Permeation Test)

First, a patch which had been cut into a 3 cm$^2$ circular shape and from which a release liner had been removed was applied to the corneum side of skin excised from a hairless mouse. Then, the skin was set to a flow-through diffusion cell kept at 32° C., so that the dermis side of the skin was located on the receptor chamber side. A phosphate buffer saline (32° C.) was introduced into the receptor chamber at a flow volume of approximately 3 ml per hour. Sample liquids were collected from the receptor chamber every 2 hours for 24 hours. Each of the collected sample liquids was quantified for the concentration of the drug (asenapine) by high-performance liquid chromatography. A skin permeation amount of asenapine was calculated according to the following formula:

skin permeation amount (μg/cm$^2$)=[drug concentration (μg/ml)×flow volume (ml)]/patch area (cm$^2$).

From this, a skin permeation amount per hour (skin permeation rate, Flux [μg/cm$^2$/hr]) was found.

Example 1

First, 70 parts by mass of a styrene-isoprene-styrene block copolymer (SIS), 30 parts by mass of polyisobutylene (PIB), 250 parts by mass of a petroleum-based tackifier resin (trade name: ARKON, manufactured by Arakawa Chemical Industries, Ltd.), and 60 parts by mass of liquid paraffin were mixed together. Thus, a homogeneous adhesive base agent composition was obtained. Then, 6 parts by mass of free asenapine, 2 parts by mass of disodium maleate (2Na maleate), 10 parts by mass of isopropyl palmitate (IPP), 81.75 parts by mass of the adhesive base agent composition, 0.25 parts by mass of a stabilizer as the other component in total, and an appropriate amount of toluene were mixed together. Thus, a homogeneous adhesive agent layer composition was obtained. Table 1 shows the composition of the adhesive agent layer composition (excluding toluene).

Subsequently, this adhesive agent layer composition was applied onto one surface of a 75 μm-thick polyester film (release liner) having been subjected to a releasing process in such a manner that the thickness of an adhesive agent layer after drying was 100 μm. Toluene was removed by drying at 60° C. for 20 minutes. Thus, the adhesive agent layer was formed. Thereafter, a 25 μm-thick polyester film (support layer) was laminated on a surface of the adhesive agent layer, the surface being opposite to the release liner, followed by cutting to thus obtain a patch.

Examples 2 and 3

Patches were obtained in the same manner as in Example 1, except that: each adhesive agent layer composition had a composition shown in Table 1 (excluding toluene).

Example 4

A patch was obtained in the same manner as in Example 1, except that: sodium maleate trihydrate (Na maleate trihydrate) was used in place of disodium maleate (2Na maleate), and the adhesive agent layer composition had a composition shown in Table 1 (excluding toluene).

Example 5

First, 6 parts by mass of an asenapine maleic acid salt (4.27 parts by mass in terms of free form), 1.19 parts by mass of sodium hydroxide (the number of moles of the asenapine maleic acid salt:the number of moles of sodium hydroxide=1:2), 10 parts by mass of isopropyl palmitate (IPP), 82.56 parts by mass of the adhesive base agent composition, 0.25 parts by mass of the other component, and an appropriate amount of toluene were mixed together. Thus, a homogeneous adhesive agent layer composition was obtained. Note that 100 parts by mass of the obtained adhesive agent layer composition (excluding toluene) comprised 4.27 parts by mass of the free asenapine and 2.39 parts by mass of disodium maleate. Table 1 shows the composition of the raw materials blended in the adhesive agent layer composition in this case (excluding toluene). Then, a patch was obtained in the same manner as in Example 1, except that: the above adhesive agent layer composition was used.

Example 6

An adhesive agent layer composition and a patch were obtained in the same manner as in Example 5, except that: sodium acetate was used in place of sodium hydroxide such that a mole ratio of the asenapine maleic acid salt to sodium acetate (the number of moles of the asenapine maleic acid salt:the number of moles of sodium acetate) was 1:2. Note that 100 parts by mass of the obtained adhesive agent layer composition (excluding toluene) comprised 4.27 parts by mass of the free asenapine and 2.39 parts by mass of disodium maleate. Table 1 shows the composition of the raw materials blended in the adhesive agent layer composition in this case (excluding toluene).

Comparative Example 1

A patch was obtained in the same manner as in Example 1, except that: 2Na maleate was not used, and the adhesive agent layer composition had a composition shown in Table 1 (excluding toluene).

Comparative Examples 2 to 5

Patches were obtained in the same manner as in Example 1, except that: the free asenapine was not used, and each adhesive agent layer composition had a composition shown in Table 2 (excluding toluene).

Comparative Examples 6 and 7

Patches were obtained in the same manner as in Example 1, except that: free tamsulosin was used in place of the free asenapine, and each adhesive agent layer composition had a composition shown in Table 3 (excluding toluene).

Comparative Examples 8 and 9

Patches were obtained in the same manner as in Example 1, except that: free bisoprolol was used in place of the free asenapine, and each adhesive agent layer composition had a composition shown in Table 3 (excluding toluene).

Comparative Example 10

A patch was obtained in the same manner as in Example 1, except that: an acrylic-based adhesive base agent having an OH group (DuroTak 87-4287, manufactured by Henkel Corporation) was used in place of the adhesive base agent composition, and the adhesive agent layer composition had a composition shown in Table 4 (excluding toluene).

Comparative Example 11

A patch was obtained in the same manner as in Example 1, except that: an acrylic-based adhesive base agent having a COOH group (DuroTak 87-2194, manufactured by Henkel Corporation) was used in place of the adhesive base agent composition, and the adhesive agent layer composition had a composition shown in Table 4 (excluding toluene).

Comparative Example 12

A patch was obtained in the same manner as in Example 1, except that: an acrylic-based adhesive base agent having no functional group (DuroTak 87-900A, Manufactured by Henkel Corporation) was used in place of the adhesive base agent composition, and the adhesive agent layer composition had a composition shown in Table 4 (excluding toluene).

Tables 1 to 3 show the result of the peel test conducted on the patch obtained in each of Examples and Comparative Examples, together with the composition of each adhesive agent layer composition (excluding toluene). Moreover, the percentage of improvement in adhesion force is also shown; those of Examples 1 to 6 are based on that of Comparative Example 1, and those of Comparative Examples 3 to 5 are based on that of Comparative Example 2. Note that, in Table 3, "ND" indicates that no measurement was possible due to anchoring collapse. In addition, Table 1 shows the result of the drug release test conducted on the patch obtained in each of Examples and Comparative Example, and also the percentages of improvement in the proportions released into water in Examples 1 to 6 based on that of Comparative Example 1.

As is apparent from the comparison between the adhesion force in Comparative Example 1 and the adhesion force in Comparative Example 2, incorporating a rubber-based adhesive agent and asenapine into an adhesive agent layer significantly decreases the adhesion force. Nevertheless, as is apparent from the results shown in Table 1, it was verified that the patch of the present invention suppressed a decrease in the adhesion force, exhibiting a sufficiently strong adhesion force, and that the release of asenapine from the adhesive agent layer was improved. On the other hand, as is apparent from the results shown in Table 2, merely combining a maleic acid alkali salt and a rubber-based adhesive agent rather decreases the adhesion force. Further, as is apparent from the results shown in Table 3, even when the other drugs in free forms were used in place of the free asenapine, a sufficient adhesion force was not exhibited, and no effect of improving the adhesion force owing to the maleic acid alkali salt was observed. These results verified that, in the present invention, combining free asenapine, a maleic acid alkali salt, and a rubber-based adhesive agent specifically exhibited the effect of improving the adhesion force of the adhesive agent layer.

Furthermore, the skin permeation test was conducted on the patch obtained in each of Examples and Comparative Examples. FIG. 1 is a graph showing a relation between the elapsed time from the application and the skin permeation rates of asenapine in the patches obtained in Example 1 and Comparative Examples 10 to 12. As is apparent from the result shown in FIG. 1, it was verified that the patch of the present invention was excellent in skin permeability of asenapine. On the other hand, it was verified that when the acrylic-based adhesive agents were used as the adhesive base agent, a sufficient skin permeability of asenapine was not exhibited. Moreover, when the acrylic-based adhesive agents were used as the adhesive base agent, no improvement in the adhesion force of the adhesive agent layer was observed even if free asenapine was combined with the maleic acid alkali salt.

The following experimental data demonstrate that a patch comprising an adhesive agent layer comprising dibutylhydroxytoluene (in a range of 0.1% by mass to 3.0% by mass) is excellent in storage stability of the drug and the patch is prevented from being colored with time.

Examples 7 to 14 and Comparative Examples 13 to 17

Patches were obtained in the same manner as in Example 1 except that each adhesive agent layer composition had a composition shown in Tables A and B.

The following storage stability evaluation test was performed on the obtained patches. The results are shown in Tables A and B together with the composition of each adhesive agent layer composition (excluding toluene).

In Tables A and B, "Ex." means "Example", "Comp. Ex." means "Comparative Example", "SIS" means "styrene-isoprene-styrene block copolymer", "PIB" means "polyisobutylene", "BHT" means "dibutylhydroxytoluene", "BHA" means "butylated hydroxyanisole", "IPP" means "isopropyl palmitate", and ARCON (trade name, manufactured by Arakawa Chemical Industries, Ltd.) was used as "petroleum-based tackifier resin".

(Storage Stability Evaluation Test)

First, a test piece 3 $cm^2$ or 10 $cm^2$ was cut from each patch. The test piece was packaged in an aluminum packing material and hermetically sealed. It was allowed to stand and stored in a temperature and humidity testing chamber at 60° C. and a humidity of 75% for one month. After release liner was released off from the test piece, the drug (acenapine) was extracted with 10 mL of THF (tetrahydrofuran) from the adhesive layer of test piece before the storage and after one-month storage, respectively. Then, 40 mL of below Eluent was added and filtered to make sample liquids. The concentration of the drug in the adhesive layer was quantitated by a high-performance liquid chromatographic (HPLC) method for each sample liquid taken. The residual percentage (%) of the drug was calculated on the basis of the concentration of the drug (% by mass) before the storage:

Residual percentage (%)=the concentration of the drug after one-month storage/the concentration of the drug before the storage*100.

*HPLC Column: TSK-gel ODS-80Ts Eluent:methanol: 0.1% phosphoric acid (added 10 mM sodium dodecyl sulfate)=75:25

Flow rate: 1.0 mL/min

Detection: 210 nm

Temperature: 40° C.

Injection volume: 10 μL.

Further, the color appearances of the patch before the storage and after one month storage were visually observed respectively and evaluated based on the following criteria:

A: No particular change in color tone was observed,

B: Discolored after one-week storage.

Tables A and B show a patch comprising an adhesive agent layer comprising dibutylhydroxytoluene (in a range of 0.1% by mass to 3.0% by mass) is excellent in storage stability of the drug and the patch is prevented from being colored with time.

TABLE 1

| | | Comparative Example 1 (reference pharmaceutical preparation 1) | Example 1 | Example 2 | Example 3 | Example 4 | Example 5 | Example 6 |
|---|---|---|---|---|---|---|---|---|
| composition [parts by mass] | free asenapine | 6 | 6 | 6 | 6 | 6 | — | — |
| | 2Na maleate | — | 2 | 5 | 10 | — | — | — |
| | Na maleate trihydrate | — | — | — | — | 10 | — | — |
| | asenapine maleic acid salt (in terms of free form) | — | — | — | — | — | 6 (4.27) | 6 (4.27) |
| | sodium hydroxide | — | — | — | — | — | 1.19 | — |
| | sodium acetate | — | — | — | — | — | — | 2.45 |
| | IPP | 10 | 10 | 10 | 10 | 10 | 10 | 10 |
| | adhesive base agent | 83.75 | 81.75 | 78.75 | 73.75 | 73.75 | 82.56 | 82.56 |
| | balance | 0.25 | 0.25 | 0.25 | 0.25 | 0.25 | 0.25 | 0.25 |
| | total | 100 | 100 | 100 | 100 | 100 | 100 | 100 |
| evaluations | adhesion force [gF/cm] (relative to reference pharmaceutical | 766 (—) | 799 (104) | 828 (108) | 868 (113) | 830 (108) | 804 (105) | 805 (105) |

TABLE 1-continued

|  | Comparative Example 1 (reference pharmaceutical preparation 1) | Example 1 | Example 2 | Example 3 | Example 4 | Example 5 | Example 6 |
|---|---|---|---|---|---|---|---|
| preparation 1) proportion released into water [%] | 84 | 87 | 89 | 95 | — | 91 | 94 |
| (relative to reference pharmaceutical preparation 1) | (—) | (104) | (106) | (113) |  | (108) | (112) |

TABLE 2

|  |  | Comparative Example 2 (reference pharmaceutical preparation 2) | Comparative Example 3 | Comparative Example 4 | Comparative Example 5 |
|---|---|---|---|---|---|
| composition [parts by mass] | free asenapine | — | — | — | — |
|  | 2Na maleate | — | 2 | 5 | 10 |
|  | IPP | 10 | 10 | 10 | 10 |
|  | adhesive base agent composition | 89.75 | 87.75 | 84.75 | 79.75 |
|  | balance | 0.25 | 0.25 | 0.25 | 0.25 |
|  | total | 100 | 100 | 100 | 100 |
| evaluations | adhesion force [gF/cm] | 1043 | 1008 | 978 | 839 |
|  | (relative to reference pharmaceutical preparation 2) | (—) | (97) | (94) | (80) |

TABLE 3

|  |  | Comparative Example 6 | Comparative Example 7 | Comparative Example 8 | Comparative Example 9 |
|---|---|---|---|---|---|
| composition [parts by mass] | tamsulosin (free form) | 6 | 6 | — | — |
|  | bisoprolol (free form) | — | — | 6 | 6 |
|  | 2Na maleate | — | 10 | — | 10 |
|  | IPP | 10 | 10 | 10 | 10 |
|  | adhesive base agent | 83.75 | 73.75 | 83.75 | 73.75 |
|  | balance | 0.25 | 0.25 | 0.25 | 0.25 |
|  | total | 100 | 100 | 100 | 100 |
| adhesion force [gF/cm] |  | 223 | 218 | 4.8 | ND |

TABLE 4

|  |  | Comparative Example 10 | Comparative Example 11 | Comparative Example 12 |
|---|---|---|---|---|
| composition [parts by mass] | free asenapine | 6 | 6 | 6 |
|  | IPP | 10 | 10 | 10 |
|  | DuroTak 87-4287 | 83.75 | — | — |
|  | DuroTak 87-2194 | — | 83.75 | — |

TABLE 4-continued

|  | Comparative Example 10 | Comparative Example 11 | Comparative Example 12 |
|---|---|---|---|
| DuroTak 87-900A | — | — | 83.75 |
| balance | 0.25 | 0.25 | 0.25 |
| total | 100 | 100 | 100 |

TABLE A

|  | Ex. 7 | Ex. 8 | Ex. 9 | Ex. 10 | Ex. 11 | Comp. Ex. 13 | Comp. Ex. 14 | Comp. Ex. 15 | Comp. Ex. 16 |
|---|---|---|---|---|---|---|---|---|---|
| asenapine maleic acid salt (in terms of free form) | 12.00 (8.54) | 12.00 (8.54) | 12.00 (8.54) | 12.00 (8.54) | 12.00 (8.54) | 12.00 (8.54) | 12.00 (8.54) | 12.00 (8.54) | 12.00 (8.54) |
| sodium acetate | 9.80 | 9.80 | 9.80 | 9.80 | 9.80 | 9.80 | 9.80 | 9.80 | 9.80 |
| SIS | 11.72 | 11.83 | 11.80 | 11.56 | 11.40 | 11.87 | 11.72 | 11.72 | 11.72 |
| petroleum-based tackifier resin | 39.05 | 39.45 | 39.32 | 38.53 | 38.00 | 39.58 | 39.05 | 39.05 | 39.05 |
| liquid paraffin | 23.43 | 23.67 | 23.59 | 23.12 | 22.80 | 23.75 | 23.42 | 23.42 | 23.42 |
| propylene glycol monolaurate | 3.00 | 3.00 | 3.00 | 3.00 | 3.00 | 3.00 | 3.00 | 3.00 | 3.00 |
| BHT | 1.00 | 0.25 | 0.50 | 2.00 | 3.00 | — | — | — | — |
| BHA | — | — | — | — | — | — | 1.00 | — | — |
| ascorbic acid | — | — | — | — | — | — | — | 1.00 | — |
| tocopherol | — | — | — | — | — | — | — | — | 1.00 |
| total | 100 | 100 | 100 | 100 | 100 | 100 | 100 | 100 | 100 |
| Residual percentage [%] | 99.80 | 100.40 | 100.90 | 100.00 | 100.60 | 98.80 | 95.90 | 100.40 | 93.30 |
| Color appearance | A | A | A | A | A | B | B | B | B |

TABLE B

|  | Comp. Ex. 17 | Ex. 12 | Ex. 13 | Ex. 14 |
|---|---|---|---|---|
| asenapine maleic acid salt (in terms of free form) | 4.50 (3.20) | 4.50 (3.20) | 4.50 (3.20) | 4.50 (3.20) |
| sodium acetate | 3.70 | 3.70 | 3.70 | 3.70 |
| SIS | 15.50 | 15.40 | 15.40 | 15.40 |
| PIB | 6.60 | 6.60 | 6.60 | 6.60 |
| petroleum-based tackifier resin | 50.90 | 50.70 | 50.70 | 50.60 |
| liquid paraffin | 8.80 | 8.80 | 8.80 | 8.80 |
| IPP | 10.00 | 10.00 | 10.00 | 10.00 |
| BHT | — | 0.20 | 0.30 | 0.50 |
| total | 100 | 100 | 100 | 100 |
| Residual percentage [%] | 97.70 | 99.10 | 99.70 | 99.40 |
| Color appearance | B | A | A | A |

INDUSTRIAL APPLICABILITY

As described above, the present invention makes it possible to provide a patch comprising an adhesive agent layer having a sufficiently strong adhesion force, the patch being excellent in releasability and skin permeability of asenapine from the adhesive agent layer.

The invention claimed is:

1. A patch, comprising:
a support layer; and
an adhesive agent layer formed on the support layer and comprising asenapine and/or a pharmaceutically acceptable salt thereof, dibutylhydroxytoluene, an adhesive base agent, and a tackifier,
wherein the adhesive base agent is a rubber-based adhesive agent such that a mass ratio of the rubber-based adhesive agent to the tackifier is 1:6 to 1.5:1, and a content of the dibutylhydroxytoluene in the adhesive agent layer is in a range of 0.1% by mass to 3.0% by mass, and a content of the rubber-based adhesive agent in the adhesive agent layer is in a range of 10% by mass to 50% by mass.

2. The patch according to claim 1, wherein the adhesive agent layer further comprises a maleic acid alkali salt.

3. The patch according to claim 2, wherein a content of the maleic acid alkali salt in the adhesive agent layer has is in a range of 0.5% by mass to 15% by mass.

4. The patch according to claim 2, wherein the maleic acid alkali salt is at least one of disodium maleate and monosodium maleate.

5. The patch according to claim 1, wherein the adhesive agent layer includes free asenapine such that a mass ratio of the free asenapine to the rubber-based adhesive agent is 1:17 to 1:1.2.

6. The patch according to claim 5, wherein a content of the rubber-based adhesive agent in the adhesive agent layer is in a range of 12% by mass to 40% by mass.

7. The patch according to claim 5, wherein the rubber-based adhesive agent is at least one selected from the group consisting of a styrene-isoprene-styrene block copolymer, polyisobutylene, and a silicone rubber.

8. The patch according to claim 1, wherein the adhesive agent layer further comprises at least one absorption enhancer selected from the group consisting of isostearyl alcohol, capric acid, propylene glycol monolaurate, isopropyl myristate, isopropyl palmitate, lauric acid diethanolamide, propylene glycol, and polyethylene glycol.

9. The patch according to claim 3, wherein the maleic acid alkali salt is at least one of disodium maleate and monosodium maleate.

10. The patch according to claim 1, wherein the rubber-based adhesive agent is at least one selected from the group consisting of a styrene-isoprene-styrene block copolymer, polyisobutylene, and a silicone rubber.

11. The patch according to claim 2, wherein the adhesive agent layer includes free asenapine such that a mass ratio of the free asenapine to the rubber-based adhesive agent is 1:17 to 1:1.2.

12. The patch according to claim 11, wherein a content of the rubber-based adhesive agent in the adhesive agent layer is in a range of 12% by mass to 40% by mass.

13. The patch according to claim 11, wherein the rubber-based adhesive agent is at least one selected from the group consisting of a styrene-isoprene-styrene block copolymer, polyisobutylene, and a silicone rubber.

14. The patch according to claim 12, wherein the rubber-based adhesive agent is at least one selected from the group consisting of a styrene-isoprene-styrene block copolymer, polyisobutylene, and a silicone rubber.

15. The patch according to claim 3, wherein the adhesive agent layer includes free asenapine such that a mass ratio of the free asenapine to the rubber-based adhesive agent is 1:17 to 1:1.2.

16. The patch according to claim 15, wherein a content of the rubber-based adhesive agent in the adhesive agent layer is in a range of 12% by mass to 40% by mass.

17. The patch according to claim 15, wherein the rubber-based adhesive agent is at least one selected from the group consisting of a styrene-isoprene-styrene block copolymer, polyisobutylene, and a silicone rubber.

18. The patch according to claim 16, wherein the rubber-based adhesive agent is at least one selected from the group consisting of a styrene-isoprene-styrene block copolymer, polyisobutylene, and a silicone rubber.

19. The patch according to claim 4, wherein the adhesive agent layer includes free asenapine such that a mass ratio of the free asenapine to the rubber-based adhesive agent is 1:17 to 1:1.2.

20. The patch according to claim 1, wherein the adhesive agent layer includes free asenapine such that a content of the free asenapine is in a range of 2% by mass to 10% by mass.

* * * * *